United States Patent [19]
Couillard et al.

[11] Patent Number: 6,098,557
[45] Date of Patent: Aug. 8, 2000

[54] HIGH SPEED METHOD FOR PRODUCING PANT-LIKE GARMENTS

[75] Inventors: Jack L. Couillard, Menasha; Laurie Couture-Dorschner, Hortonville; Gregory J. Rajala, Neenah; James F. Roth, Appleton, all of Wis.

[73] Assignee: Kimberly-Clark Worldwide, Inc., Neenah, Wis.

[21] Appl. No.: 09/338,898

[22] Filed: Jun. 23, 1999

[51] Int. Cl.⁷ ............................... A61B 9/00; B32B 31/08
[52] U.S. Cl. ................... 112/475.06; 112/475.09; 2/400; 156/73.1; 156/204; 156/269
[58] Field of Search ................. 112/475.09, 475.06, 112/475.08, 475.01, 470.01, 470.05, 470.33; 2/400, 401, 402; 156/73.1, 164, 204, 269, 290, 297, 308.4

[56] References Cited

U.S. PATENT DOCUMENTS

| | | |
|---|---|---|
| 3,338,992 | 8/1967 | Kinney . |
| 3,341,394 | 9/1967 | Kinney . |
| 3,502,763 | 3/1970 | Hartmann . |
| 3,542,615 | 11/1970 | Dobo et al. . |
| 3,604,015 | 9/1971 | Dove ............................................ 2/402 |
| 3,692,618 | 9/1972 | Dorschner et al. . |
| 3,802,817 | 4/1974 | Matsuki . |
| 3,849,241 | 11/1974 | Butin et al . |
| 4,041,203 | 8/1977 | Brock et al. . |
| 4,327,448 | 5/1982 | Lunt . |
| 4,340,563 | 7/1982 | Appel et al. . |
| 4,388,075 | 6/1983 | Mesek et al. . |
| 4,405,297 | 9/1983 | Appel et al. . |
| 4,606,964 | 8/1986 | Wideman . |
| 4,639,949 | 2/1987 | Ales et al. . |
| 4,657,802 | 4/1987 | Morman . |
| 4,704,116 | 11/1987 | Enloe . |
| 4,720,415 | 1/1988 | Vander Wielen et al. . |
| 4,798,603 | 1/1989 | Meyer et al. . |
| 4,938,753 | 7/1990 | Van Gompel et al. . |
| 4,938,754 | 7/1990 | Mesek . |
| 4,940,464 | 7/1990 | Van Gompel et al. . |
| 5,034,007 | 7/1991 | Igaue et al. .......................... 156/269 X |

(List continued on next page.)

FOREIGN PATENT DOCUMENTS

| | | |
|---|---|---|
| 539 703 | 5/1993 | European Pat. Off. . |
| 586 924 | 3/1994 | European Pat. Off. . |
| 2 284 741 | 6/1995 | United Kingdom . |
| 95/18589 | 7/1995 | WIPO . |
| 96/03949 | 2/1996 | WIPO . |
| 96/03950 | 2/1996 | WIPO . |
| 97/18785 | 5/1997 | WIPO . |

OTHER PUBLICATIONS

Manson, John A. and Sperling, Leslie H., Polymer Blends & Composites, Plenum Press, a division of Plenum Publishing Corp., New York, New York, pp. 273–277 (1976).

*Primary Examiner*—Peter Nerbun
*Attorney, Agent, or Firm*—Pauley Petersen Kinne & Fejer

[57] ABSTRACT

A method for producing a pant-type garment in which a first substantially rectangular fabric layer is placed on top of a second substantially rectangular fabric layer. The first substantially rectangular fabric layer is joined to the second substantially rectangular fabric layer, forming a multi-layer fabric. A crescent-shaped cutout section is cutout from the opposed multi-layer fabric edges of the multi-layer fabric, forming opposed tabs at each end of the opposed multi-layer fabric having a first tab and a second tab. The multi-layer fabric is cut transversely in half, forming two multi-layer fabric halves. Each of the multi-layer halves is folded longitudinally and the first tab and the second tab on one side of each of the multi-layer fabric halves is joined to the corresponding first tab and second tab on the opposed side of each respective multi-layer fabric half, forming two outside-in pant-like garments.

24 Claims, 5 Drawing Sheets

U.S. PATENT DOCUMENTS

| | | |
|---|---|---|
| 5,057,368 | 10/1991 | Largman et al. . |
| 5,069,970 | 12/1991 | Largman et al. . |
| 5,108,820 | 4/1992 | Kaneko et al. . |
| 5,108,827 | 4/1992 | Gessner . |
| 5,110,403 | 5/1992 | Ehlert . |
| 5,114,781 | 5/1992 | Morman . |
| 5,116,662 | 5/1992 | Morman . |
| 5,145,727 | 9/1992 | Potts et al. . |
| 5,169,706 | 12/1992 | Collier, IV et al. . |
| 5,178,931 | 1/1993 | Perkins et al. . |
| 5,188,885 | 2/1993 | Timmons et al. . |
| 5,277,976 | 1/1994 | Hogle et al. . |
| 5,336,552 | 8/1994 | Strack et al. . |
| 5,340,424 | 8/1994 | Matsushita . |
| 5,466,410 | 11/1995 | Hills . |
| 5,711,832 | 1/1998 | Glaug et al. ................... 156/269 X |
| 5,716,478 | 2/1998 | Boothe et al. . |

HIGH SPEED METHOD FOR PRODUCING PANT-LIKE GARMENTS

FIELD OF THE INVENTION

This invention relates to a method for producing pant-type garments such as swimming trunks, training pants, disposable underwear, shorts, surgical pants and the like. More particularly, this invention relates to a high speed method for producing such pant-type garments at diaper machine speeds (in excess of about 600 per minute).

DESCRIPTION OF RELATED ART

Typically, production of pant-type garments such as swimming trunks and disposable incontinence garments such as training pants is a relatively complex process requiring a multitude of operating steps, including manual steps such as the sewing of seams, in order to arrive at a completed product. As a result, production speeds are relatively slow.

Accordingly, it is one object of this invention to provide a method for producing pant-type garments which eliminates manual steps required by conventional production methods.

It is another object of this invention to provide a method for producing pant-type garments capable of producing such garments at production speeds in excess of about 600 garments per minute.

SUMMARY OF THE INVENTION

These and other objects of this invention are addressed by a method for producing pant-type garments in which a first substantially rectangular fabric layer is placed on top of a second substantially rectangular fabric layer, in which the first substantially rectangular fabric layer is narrower than the second substantially rectangular fabric layer, as a result of which the two opposed edges of the second substantially rectangular fabric layer extends beyond the corresponding opposed edges of the first substantially rectangular fabric layer. The corresponding opposed edges of the first substantially rectangular fabric layer and the second substantially rectangular fabric layer are joined together, forming a multi-layer fabric. In accordance with one preferred embodiment, the edges are joined together by crescent-shaped, U-shaped, or similarly shaped bonds. Crescent-shaped, U-shaped or similarly shaped cutout sections are cut out from the opposed, joined multi-layer fabric edges of the multi-layer fabric, forming opposed tabs at each end of the opposed edges of the multi-layer fabric, each of which opposed tabs comprises a long tab and a short tab. Preferably, the cutout sections are cut out proximate the crescent-shaped, U-shaped or similarly shaped bonds along the side of the bonds facing the edges of the multi-layer fabric. The multi-layer fabric is then cut transversely in half, forming two multi-layer fabric halves. Each of the multi-layer halves is folded longitudinally and the long tab and the short tab on one side of each multi-layer fabric half is joined to a corresponding long tab and short tab on the opposed side of each said multi-layer fabric half, forming an outside-in pant-type garment. It will be apparent to those skilled in the art that the last two steps may be carried out in reverse order, that is the multi-layer fabric being folded longitudinally in half and the long tabs and the short tabs of the opposed tabs of the multi-layer fabric being joined together after which the folded multi-layer fabric layer is cut transversely in half, to form two outside-in pant-type garments.

In accordance with one preferred embodiment of the method of this invention, each of the substantially rectangular fabric layers comprises two fabric layer halves longitudinally joined together. In accordance with one embodiment, at least one of the fabric layer halves has a different color from the remaining fabric halves, as a result of which multi-colored pant-type garments are produced.

In order to convert the method of this invention to a continuous process for which production speeds in excess of 600 pieces per minute can be achieved, continuous web materials are employed whereby a narrower continuous first material web having first material edges is deposited on to a wider continuous second material web having second material edges which extend beyond the corresponding first material edges. The first material web is joined to the second material web with crescent-shaped, U-shaped or similarly shaped bonds, forming a multi-layer web having opposed edges. A plurality of corresponding pairs of crescent-shaped cutout sections are cut out from the opposed edges of the multi-layer material, each of which pair of corresponding crescent-shaped cutout sections is spaced apart from an adjacent said corresponding pair, forming opposed tabs between each of said corresponding pairs of crescent-shaped cutout sections along a length of the multi-layer material web, each of which opposed tabs comprises a long tab and a short tab. The multi-layer material web is folded along a longitudinal centerline and the long tab and the short tab of one of said opposed tabs is joined to a respective long tab and short tab of the other opposed tab, forming a folded multi-layer material web. The folded multi-layer material web is cut transversely along a first transverse line bisecting said joined opposed tabs and along a second transverse line bisecting the crescent-shaped bonded substantially instantaneous wettability cutout sections, producing a plurality of inside-out pant-type garments.

In accordance with either the batch or continuous method of producing pant-type garments in accordance with this invention, the outside-in pant-type garment may be left outside-in for turning inside-out by the consumer, thereby guaranteeing the freshness and cleanliness of the outside of the garment. Alternatively, the outside-in pant-type garment may be turned inside-out as an additional step to the method of this invention.

BRIEF DESCRIPTION OF THE DRAWINGS

These and other objects and features of this invention will be better understood from the following detailed description taken in conjunction with the drawings wherein.

DETAILED DESCRIPTION OF PREFERRED EMBODIMENTS

Definitions

As used herein, the term "nonwoven web" means a web having a structure of individual fibers or threads which are interlaid, but not in an identifiable manner, as in a knitted fabric. Nonwoven fabrics or webs have been formed from many processes such as, for example, spunbonding processes, meltblowing processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91).

As used herein, the term "spunbond fibers" refers to small diameter fibers which are formed by extruding molten thermoplastic material as filaments from a plurality of fine, usually circular capillaries of a spinneret, with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 30 microns. The fibers may also have shapes such as those described in U.S. Pat. No. 5,277,976 to Hogle et al., U.S. Pat. No. 5,466,410 to Hills, and U.S. Pat. No. 5,069,970 and U.S. Pat. No. 5,057,368 to Largman et al., which describe hybrids with unconventional shapes. A nonwoven web of spunbond fibers produced by melt spinning is referred to as a "spunbond".

As used herein, the term "meltblown fibers" means fibers formed by extruding a molten thermoplastic material through a plurality of fine, usually circular, die capillaries as molten threads or filaments into converging high velocity, usually hot, gas (for example, air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, by U.S. Pat. No. 3,849,241 to Butin et al. Meltblown fibers are microfibers which may be continuous or discontinuous, are generally smaller than 10 microns in average diameter, and are generally tacky when deposited onto a collecting surface.

As used herein, the term "bonded carded web" refers to webs made from staple fibers which are sent through a combing or carding unit, which breaks apart and aligns the staple fibers in the machine direction to form a generally machine direction-oriented fibrous nonwoven web. Such fibers are usually purchased in bales which are placed in a picker which separates the fibers prior to the carding unit. Once the web is formed, it is then bonded by one or more of several known bonding methods.

As used herein, the term "bicomponent fibers" refers to fibers which have been formed from at least two polymers extruded from separate extruders but spun together to form one fiber. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another or may be a side-by-side arrangement or an "islands-in-the-sea" arrangement. Bicomponent fibers are taught in U.S. Pat. No. 5,108,820 to Kaneko et al., U.S. Pat. No. 5,336,552 to Strack et al., and European Patent 0586924. For two component fibers, the polymers may be present in ratios of 75/25, 50/50, 2/75 or any other desired ratios.

As used herein, the term "biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation, New York, N.Y., IBSN 0-306-30831-2, at pages 273 through 277.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" also includes all possible geometric configurations of the molecule. These configurations include, but are not limited to, isotactic, syndiotactic and random symmetries.

The invention disclosed and claimed herein is a method for high-speed production of pant-type garments such as shorts, pants, disposables such as training pants, incontinence garments and underwear, as well as surgical pants and the like. The method may be employed either as a batch process or as a continuous process as described hereinbelow. Materials suitable for use in the method of this invention include, but are not limited to, cotton, knits, woven materials and nonwoven materials. Base materials suitable for use in the method of this invention are preferably selected from the group consisting of spunbond, meltblown, spunbond-meltblown-spunbond laminates, coform, spunbond-film-spunbond laminates, bicomponent spunbond, bicomponent meltblown, biconstituent spunbond, biconstituent meltblown, pulp, superabsorbent, bonded carded web and combinations thereof.

Figure 1:
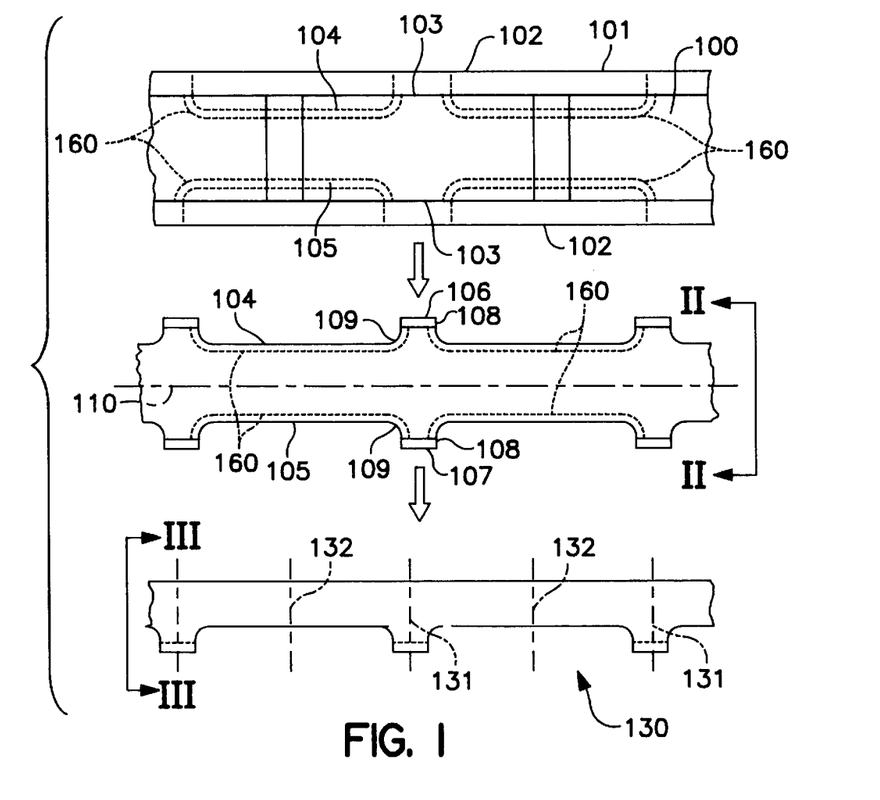
FIG. 1 is a schematic flow diagram showing the basic material processing steps of the method of this invention.
Figure 2:
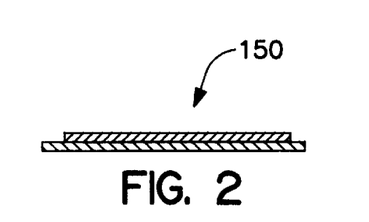
FIG. 2 is a cross-sectional view of the material in the second stage of processing taken along the line II—II in FIG. 1.
Figure 3:
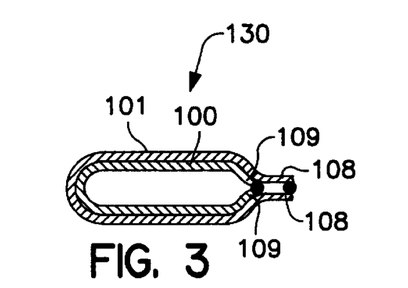
FIG. 3 is a cross-sectional view of the material in the third stage of processing taken along the line III—III in FIG. 1.
Figure 3A:
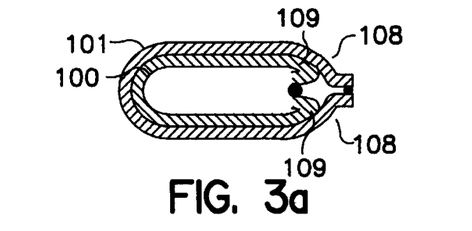
FIG. 3a is a cross-sectional view of the material in the third stage of processing taken along line III—III in FIG. 1 in accordance with an alternative embodiment of the method of this invention.

The continuous method for producing pant-type garments in accordance with one embodiment of this invention, as generally shown in FIGS. 1–3, comprises the steps of depositing a narrower continuous first material web 100 having first material edges 103 on top of a wider continuous second material web 101 having second material edges 102, whereby the second material edges 102 extend beyond the corresponding first material edges 103. The continuous first material web 100 is joined to the second material web 101 by a series of crescent-shaped, U-shaped, or similarly shaped bonds 160 along the material edges 102, 103, forming a multi-layer material web 150 having opposed edges. Joining of the first material web 100 to the second material web 101 may be accomplished by any suitable bonding means known to those skilled in the art including, but not limited to, ultrasonic bonding, thermal bonding, mechanical fasteners and sewing, although in the latter case, the speed of the method of this invention may be lower than for the use of the ultrasonic or thermal bonding methods. Thereafter, a plurality of corresponding pairs of cutout sections 104, 105, preferably crescent-shaped, U-shaped or similarly shaped, are cut out from the opposed edges of the multi-layer material web on the material edge side of the bonds, each of the corresponding pairs being spaced apart from an adjacent corresponding pair, thereby forming opposed tabs 106, 107 between each of the corresponding pairs along a length of the multi-layer material web. Each of the opposed tabs 106, 107 comprises a long tab 108 and a short tab 109. The multi-layer material web is folded along its longitudinal centerline 110. It will be apparent to those skilled that the order in which these steps are performed may be reversed. That is, the cutouts 104, 105, may be made after folding along the centerline 110 along the free edges opposite centerline 110, thereby creating the cutout sections 104, 105 simultaneously. The short tab and the long tab of one of the opposed tabs are joined to the respective short tab and long tab of the other opposed tab, forming a folded multi-layer material web 130. Alternatively, as shown in FIG. 3a, the short tabs may first be folded over prior to bonding so as to face the interior of the folded multi-layer material web 130, thereby producing a more tailored looking garment. If this alternate execution is used, the two material webs 100, 101 can be the same width because the act of folding makes the top material web 101 narrower. The folded multi-layer material web 130 is then cut transversely along a first transverse line 131 bisecting the joined opposed tabs and along a second transverse line 132 bisecting the crescent-shaped cutout sections 104, 105, producing a plurality of inside-out pant-type garments. The inside-out pant-type garments may be turned outside-in or they may be left inside-out.

Figure 4A:
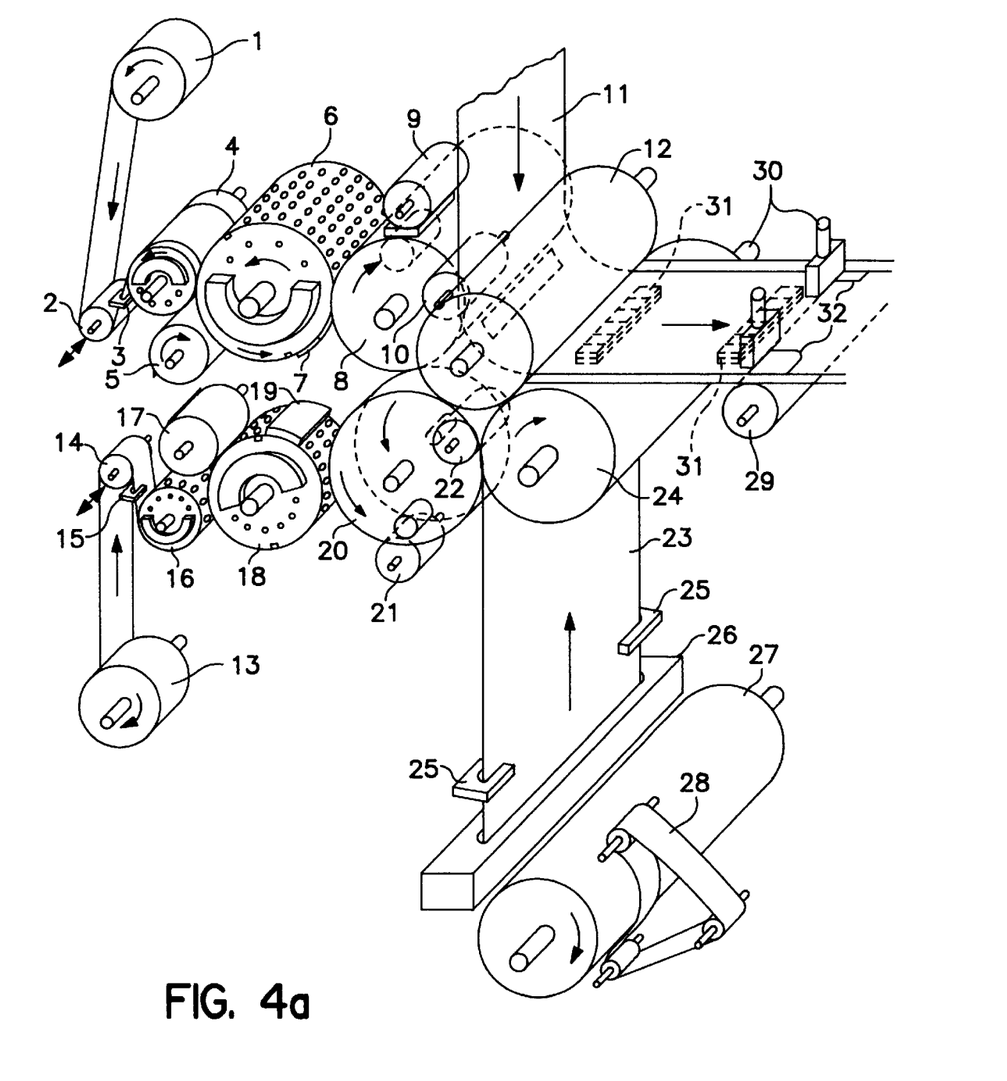
FIGS. 4a–4d show a schematic diagram, including a process apparatus, of a method for producing pant-type garments in accordance with one embodiment of this invention.

FIG. 4a is a diagram of a process apparatus for producing pant-type garments in accordance with the method of this invention. Waistband material is unwound from a tension controlled unwind 1 onto web guiding roll 2 controlled by sensor(s) 3. In accordance with one preferred embodiment, the waistband material is an elastic material. Alternatively, the waistband material may include a drawstring or elastic cord in place of the elastic material. Vacuum feed roll 4 meters the waistband material. If the waistband is to be one inch wide, vacuum feed roll 4 meters two inches for every two end products since the waistband material is cut in half at the final cutoff. The waistband material is conveyed onto vacuum anvil roll 6 on which it is cut by knife roll 5 into discrete pieces 7 and transferred into an applicator. As shown, the waistband is spread by two diverging disks 8 which hold the waistband material with pins, vacuum, or mechanical means such as tenter frame clips. However, any spreading method known to those skilled in the art is acceptable. Glue applicator 9 applies stripes of a hot melt glue on the expanded waistband. Alternatively, an ultrasonic bonder may be employed at this stage to ultrasonically bond the waistband. It will be apparent to those skilled in the art that any suitable bonding method may be employed for bonding of the waistband. Nip roll 10 is disposed inside of the diverging disks 8 and nips the glue stripes on the waistband piece 7 to material web 11. Roll 12 acts as a backup/turning roll. Narrow top material web 11 is unwound by a tension controlled unwind (not shown). Narrow top material web 11 may be a single color or a print. In addition, it may be made from two or more material webs bonded upstream if a multicolored or multi-textured finished is desired. Turning/backup roll 12 turns material web 11 and acts as a backup for nip roll 10, which attaches waistband strips 7 to material web 11. Reference numerals 13–22 refer to the same process described above with the exception that it applies to a second wider material web 23 from roll 27. The two waistbands are registered to each other and to material webs 11 and 23. Turning/backup roll 24 functions similar to turning/backup roll 12. Sensors 25 are used to control web guide 26 which controls the cross machine position of material web 23. The unwind for the wider material web 23 is driven by belt 28; however, other types of unwinds, such as a drum or a center (core) driven unwind, may also be employed. Anvil roll 29 is a pattern bonder which applies waist bond patterns, for example crescent-shaped, U-shaped or similarly shaped bonds, in combination with ultrasonic horns 30. Although shown as stationary horns, ultrasonic horns 30 may be rotary horns. See, for example, U.S. Pat. Nos. 5,707,470 and 5,711,847 which describe the use of ultrasonic horns for bonding of materials. At this point, two waistband pieces 31, comprising a combination of waistbands 7 and 19, are sandwiched between narrower material web 11 and wider material web 23. Continuous or non-continuous waist seam bonds 32 are applied to webs resulting in attachment of the waistbands to the material webs 11 and 23. To produce a fly, if desired, the bonds 32 can be interrupted.

Figure 4B:
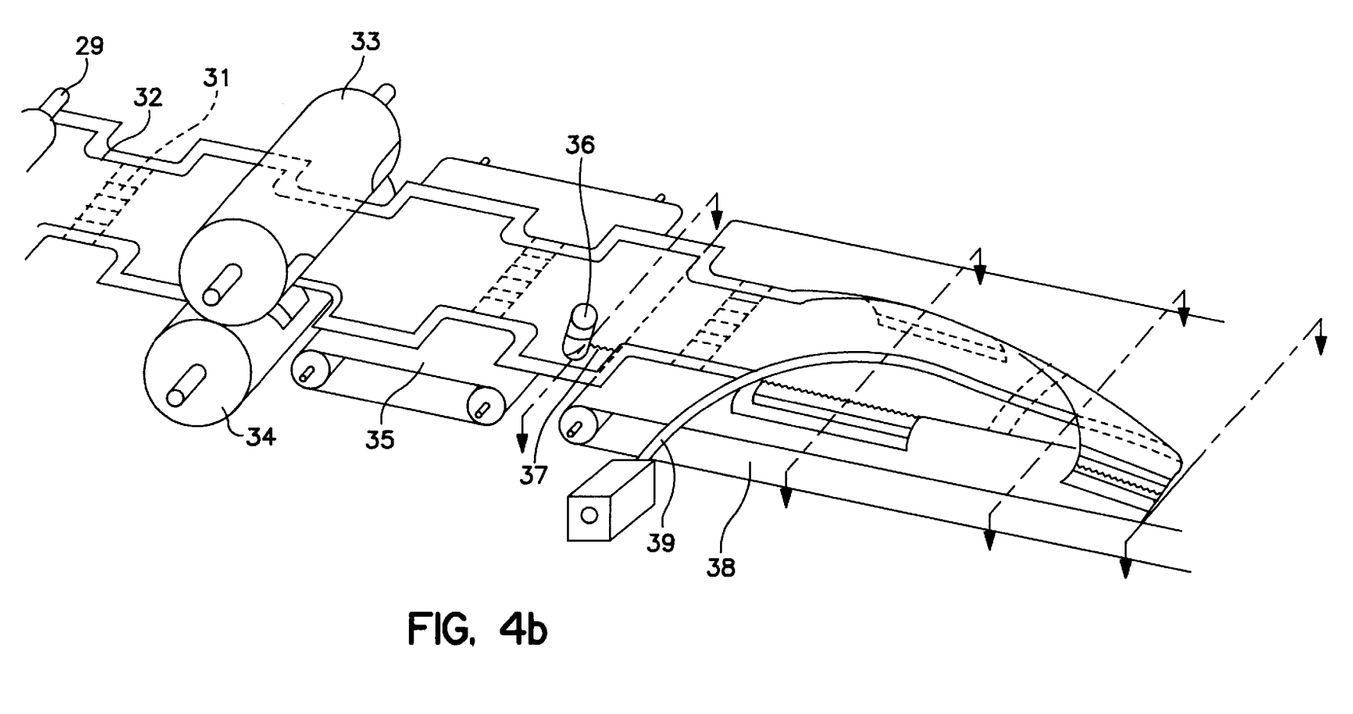
Figure 4C:
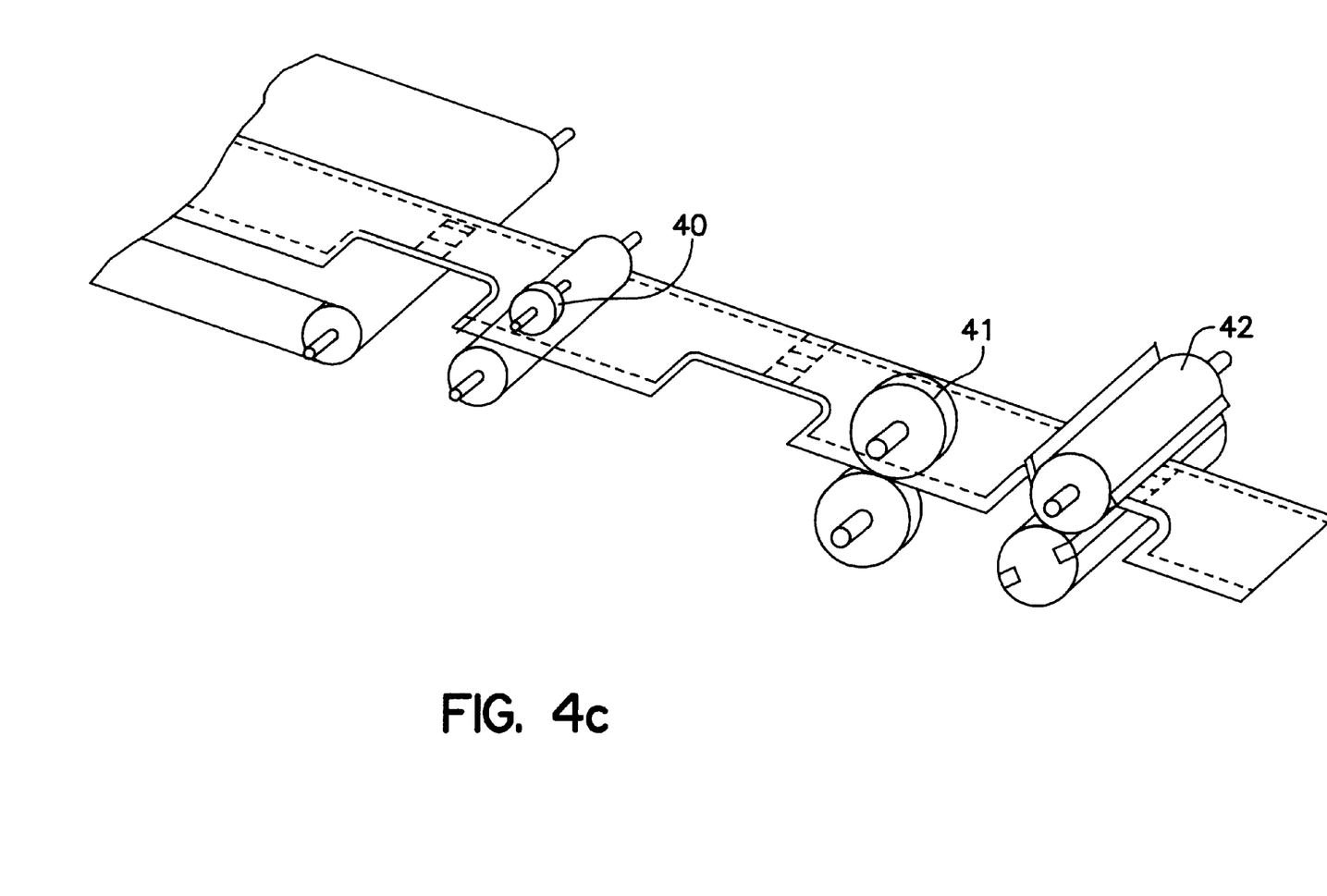
Figure 4D:
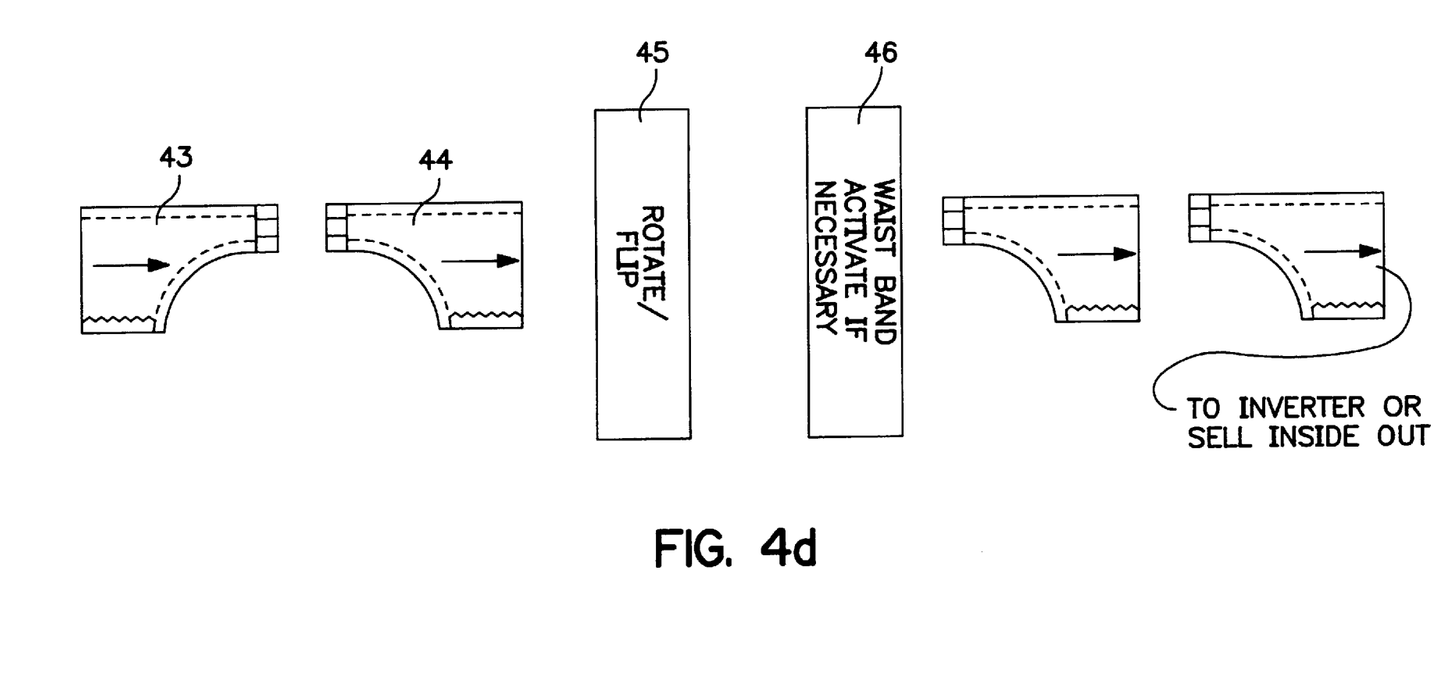

FIG. 4b is a continuation of the apparatus of FIG. 4a. Rotary die roll 33 and rotary anvil roll 34 cut out the crescent-shaped cutout sections along waist seam bonds 32. Such cutting may be carried out by any method known to those skilled in the art, but is preferably carried out by die cutting, water-jet cutting, laser cutting or slitting. Vacuum transport conveyer 35 conveys the web beneath intermittent glue applicator 36 which applies a glue line 37 to one of the opposed tabs formed by the cutout of the crescent-shaped cutout sections (between the cutout sections). The web is then folded along its longitudinal centerline by folding conveyor 38 comprising folding rod 39. As shown in FIG. 4c which is a continuation of FIG. 4b, nip section 40 seals the smaller opposed tabs of the narrow material web 11 to each other at the previously applied glue line 37. Rotary ultrasonic bonder 41 ultrasonically bonds the long opposed tabs of the wider material web 23 to each other after which the web is cut by cutter 42 at the middle of the waistband and the middle of the tab sections (corresponding to the leg portion of the final product). As shown in FIG. 4d, the cut product alternates between the waistband leading 43 and the leg portion leading 44. As a result, there are at least two alternative steps for further processing. Either every other product can be rotated by rotator 45, or the products can be separated into two separate product streams. Thereafter, if a latent waistband material has been used, it is activated at point 46. Thereafter, the product may be turned inside out by an inverter, or alternatively it may be sold without inverting it.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A method for producing a pant-type garment comprising the steps of:
   placing a first substantially rectangular fabric layer on top of a second substantially rectangular fabric layer;
   joining said first substantially rectangular fabric layer to said second substantially rectangular fabric layer, forming a multi-layer fabric having opposed multi-layer fabric edges and having joined regions corresponding to a cutout section of each of said opposed multi-layer fabric edges;
   cutting out said cutout section from each of said opposed multi-layer fabric edges of said multi-layer fabric on a side of said joined regions disposed towards each of said opposed multi-layer fabric edges, forming opposed tabs at each end of said opposed multi-layer fabric, each of said opposed tabs comprising a first tab and a second tab;

cutting said multi-layer fabric transversely in half, forming two multi-layer fabric halves;

folding one of said multi-layer halves longitudinally; and joining said first tab and said second tab on one side of said one of said multi-layer fabric halves to the corresponding said first tab and said second tab on the opposed side of said one of said multi-layer fabric halves, forming an outside-in pant-like garment.

2. A method in accordance with claim 1, wherein said first substantially rectangular fabric layer is narrower than said second substantially rectangular fabric layer and said first tabs are shorter than said second tabs.

3. A method in accordance with claim 1, wherein said first substantially rectangular fabric layer is equal in width to said second substantially rectangular fabric layer and said first tabs are equal in length to said second tabs.

4. A method in accordance with claim 1, wherein said cutout section has one of a crescent shape and a U-shape.

5. A method in accordance with claim 1 further comprising turning said outside-in pant-like garment inside-out.

6. A method in accordance with claim 1, wherein said fabric is a material selected from the group consisting of cotton, knits, wovens, nonwovens and combinations thereof.

7. A method in accordance with claim 1, wherein said joining of said first substantially rectangular fabric layer to said second substantially rectangular fabric layer and said joining of said tabs are carried out by a method selected from the group consisting of ultrasonic bonding, thermal bonding, adhesive bonding, sewing, mechanical fasteners and combinations thereof.

8. A method in accordance with claim 1, wherein said cutting of said cutout sections is achieved by a method selected from the group consisting of die cutting, water-jet cutting, laser cutting and slitting.

9. A method in accordance with claim 1, wherein each of said substantially rectangular fabric layers comprises two fabric layer halves longitudinally joined together.

10. A method in accordance with claim 9, wherein at least one of said fabric layer halves has a different color than the remaining said fabric layer halves.

11. A method in accordance with claim 1, wherein a waistband material is joined to said multi-layer fabric, said waistband positioned transversely with respect to said multi-layer fabric and extending between opposed said cutout sections.

12. A continuous method for producing a pant-type garment comprising the steps of:

depositing a continuous first material web having first material edges on top of a continuous second material web having second material edges;

joining said first material web to said second material web, forming a multi-layer material web having opposed multi-layer edges and having joined regions corresponding to a cutout section of each of said opposed multi-layer edges;

cutting out a plurality of corresponding pairs of said cutout sections from each of said opposed multi-layer edges of said multi-layer material, each of said corresponding pairs being spaced apart from an adjacent said corresponding pair, forming opposed tabs between each of said corresponding pairs along a length of said multi-layer material web, each of said opposed tabs comprising a first tab and a second tab;

folding said multi-layer material web along a longitudinal centerline;

joining said first tab and said second tab of one of said opposed tabs to the respective first tab and second tab of the other said opposed tab, forming a folded multi-layer material web; and cutting said folded multi-layer material web transversely along a first transverse line bisecting said joined opposed tabs and along a second transverse line bisecting said cutout sections, producing a plurality of outside-in pant-like garments.

13. A method in accordance with claim 12, wherein said continuous first material web is narrower than said continuous second material web and said first tabs are shorter than said second tabs.

14. A method in accordance with claim 12, wherein said continuous first material web is equal in width to said continuous second material web and said first tabs are equal in length to said second tabs.

15. A method in accordance with claim 12, wherein said first material web and said second material web each comprise longitudinally joined continuous web halves.

16. A method in accordance with claim 15, wherein at least one of said web halves has a different color than said other web halves.

17. A method in accordance with claim 12 further comprising turning each of said outside-in pant-like garments inside-out.

18. A method in accordance with claim 12, wherein said material webs comprise a material selected from the group consisting of cotton, knits, wovens, nonwovens and combinations thereof.

19. A method in accordance with claim 12, wherein said joining of said first material web to said second material web and said joining of said tabs are carried out by a method selected from the group consisting of ultrasonic bonding, thermal bonding, adhesive bonding, mechanical fasteners, sewing and combinations thereof.

20. A method in accordance with claim 12, wherein said cutting of said crescent-shaped cutout sections is achieved by a method selected from the group consisting of die cutting, water-jet cutting, laser cutting and slitting.

21. A method in accordance with claim 12, wherein a waistband material is joined to said multi-layer material web, said waistband material extending transversely across said multi-layer material web and bisecting said cutout sections.

22. A method in accordance with claim 12, wherein said first material edges are joined to said second material web using a joining pattern corresponding to said cutout sections.

23. A method in accordance with claim 12, wherein said material webs are nonwovens selected from the group consisting of spunbond, meltblown, films, bonded carded and combinations thereof.

24. A continuous method for producing a pant-type garment comprising the steps of:

depositing a continuous first material web having first material edges on top of a continuous second material web having second material edges;

joining said first material web to said second material web, forming a multi-layer material web having opposed multi-layer edges and having joined regions corresponding to a cutout section of each of said opposed multi-layer edges;

folding said multi-layer material web along a longitudinal centerline;

cutting out a plurality of corresponding pairs of said cutout sections from each of said opposed multi-layer edges of said multi-layer material, each of said corresponding pairs being spaced apart from an adjacent said corresponding pair, forming opposed tabs between each of said corresponding pairs along a length of said multi-layer material web, each of said opposed tabs comprising a first tab and a second tab;

joining said first tab and said second tab of one of said opposed tabs to the respective first tab and second tab of the other said opposed tab, forming a folded multi-layer material web; and cutting said folded multi-layer material web transversely along a first transverse line bisecting said joined opposed tabs and along a second transverse line bisecting said cutout sections, producing a plurality of inside-out pant-like garments.

\* \* \* \* \*